United States Patent
Bill et al.

[11] Patent Number: 6,045,761
[45] Date of Patent: Apr. 4, 2000

[54] PROCESS AND DEVICE FOR THE CONVERSION OF A GREENHOUSE GAS

[75] Inventors: Alain Bill, Baden; Baldur Eliasson, Birmenstorf; Eric Killer, Wettingen; Ulrich Kogelschatz, Hausen, all of Switzerland

[73] Assignee: ABB Research Ltd., Zurich, Switzerland

[21] Appl. No.: 08/930,915

[22] PCT Filed: Feb. 11, 1997

[86] PCT No.: PCT/CH97/00042

§ 371 Date: Oct. 14, 1997

§ 102(e) Date: Oct. 14, 1997

[87] PCT Pub. No.: WO97/29833

PCT Pub. Date: Aug. 21, 1997

[30] Foreign Application Priority Data

Feb. 15, 1996 [DE] Germany .............. 196 05 547
May 30, 1996 [DE] Germany .............. 196 21 653

[51] Int. Cl.[7] .............. B01J 19/08; F01N 3/10; F28D 8/04; C01B 21/00; H05F 3/00
[52] U.S. Cl. .............. 422/186.04; 422/173; 422/174; 422/186.21; 422/186.23; 422/198; 422/199; 423/235; 204/164
[58] Field of Search .............. 423/219, 235, 423/240 R, 245.1, 246; 204/164, 165, 168, 169, 170, 176, 177, 178, 179; 422/186.04, 186.21, 186.23, 174, 199, 173, 198

[56] References Cited

U.S. PATENT DOCUMENTS

| | | | |
|---|---|---|---|
| 3,703,460 | 11/1972 | Shair et al. ............. | 204/327 |
| 3,875,034 | 4/1975 | Adams et al. ............ | 204/165 |
| 4,374,288 | 2/1983 | Scragg .................... | 568/910 |
| 4,780,277 | 10/1988 | Tanaka et al. ............ | 422/4 |
| 5,047,127 | 9/1991 | Tottori et al. ............ | 204/176 |

FOREIGN PATENT DOCUMENTS

| | | |
|---|---|---|
| 9471624 | 9/1993 | Australia . |
| 9471624 | 4/1995 | Australia ............ C07C 31/04 |

(List continued on next page.)

OTHER PUBLICATIONS

Henely et al., Equilibrium–Stage Separation Operations in Chemical Engineering, Wiley & Sons, p. 7–8, 1981.

"Conversion du $CO_2$ en CO par decharge couronne dans des melanges air–$CO_2$", Boukhalfa, et al., Rev. Int. Hautes Temper. Refract., 1990, 26, 39–48.

"Direct Conversion from Methane to Methanol by a Pulsed Silent Discharge Plasma", Okazaki, et al., 12th International Symposium on Plasma Chemistry, vol. 11, 1995, pp. 581–586.

"Modeling and Applications of Silent Discharges Plasmas", Eliasson, et al., IEEE Transactions on Plasma Science, vol. 19, No. 2, Apr. 1991, pp. 309–323.

*Primary Examiner*—Steven P. Griffin
*Assistant Examiner*—Maribel Medina
*Attorney, Agent, or Firm*—Burns, Doane, Swecker & Mathis, L.L.P.

[57] ABSTRACT

So that fuels can be produced efficiently from an undesirable greenhouse gas, the gas is subjected, together with a catalyst gas, preferably nitrogen or nitrous oxide, and a hydrogen-containing gas or vapour, to a silent electric discharge in a 1st reactor (4). In the process, excited or ionized atoms and/or molecules are formed which are converted, in a catalyst reactor (8) comprising a copper-containing 1st catalyst (8'), to $H_2$ and possibly CO. Via an expansion valve (9), a liquid (13) separates from a fuel in a liquid vessel (11). Gases escaping from the liquid vessel (11) are passed over a thermal reactor (14) containing a 2nd catalyst (15) and expanded via an expansion valve (16). In a downstream liquid vessel (11') $CH_3OH$, for example, separates as the desired liquid fuel (13'). The 1st reactor (4) and the thermal reactor (14) may be combined in a container comprising a plurality of reaction chambers which are parallel to one another.

4 Claims, 1 Drawing Sheet

FOREIGN PATENT DOCUMENTS

| | | | |
|---|---|---|---|
| 2713511 | 6/1995 | France | B01J 7/00 |
| 2357392 | 5/1975 | Germany | B01J 19/08 |
| 260011A1 | 9/1988 | Germany | B01J 19/00 |
| 4220865 | 2/1993 | Germany . | |
| 4220865A1 | 2/1993 | Germany | C25B 3/04 |
| 4231581A1 | 3/1994 | Germany | A62D 3/00 |
| 4332790A1 | 3/1995 | Germany | C07C 29/154 |
| 4-135637 | 5/1992 | Japan | B01J 19/08 |
| WO93/19838 | 10/1993 | WIPO | B01D 53/36 |

PROCESS AND DEVICE FOR THE CONVERSION OF A GREENHOUSE GAS

This application is a National Stage of International Application No. PCT/CH97/00042, filed Feb. 11, 1997.

BACKGROUND OF THE INVENTION

1. Field of the invention

The invention is based on a process and an apparatus for converting a greenhouse gas into a chemically or industrially utilizable substance or into a chemically or industrially utilizable mixture of substances.

2. Discussion of Background

The precharacterizing clauses of the claims of the invention relate to a prior art as is disclosed by DE 4 220 865 A1. There carbon dioxide, $CO_2$, admixed with a substance containing hydrogen atoms, such as e.g. hydrogen gas, $H_2$, water, $H_2O$, or hydrogen sulphide, $H_2S$, is subjected in a reactor to silent electric discharges which produce the fuels methane, $CH_4$, and/or methanol, $CH_3OH$. The reactor contains a reaction accelerator in the form of a catalyst which contains copper and, if required, one or more of the metals Zn, Al, Mn, Cr, Ag, Mo, Ni or V. The catalyst may have been applied to a dielectric, to an electrode, to glass wool, quartz wool or rock wool, to $ZrO_2$, $Al_2O_3$, zeolite, silica gel or granular materials.

DE 4 332 790 A1 discloses a process for producing methanol from carbon dioxide and hydrogen in a thermal reactor which, in its bottom region, contains a copper-based catalyst. The temperature in the reaction chamber is between 220 and 250° C., the pressure between 100 kPa and 2 MPa, the reaction mixture having a molar ratio of hydrogen to carbon dioxide in the range of from 1:1 to 1:10, preferably of 1:3. The residence time of the reaction mixture in the reaction chamber is between 0.1 s and 10 s, preferably 1 s.

These processes are not sufficiently efficient and, if hydrogen is used as the starting reactant, are still relatively expensive.

N. Boukhalfa et al., Conversion du $CO_2$ en CO par décharge couronne dans des mélanges air-$CO_2$, Rev. Int. Hautes Tempér. Refract. 26 (1990), pp. 39–48, disclose the acceleration of the conversion of $CO_2$ into CO in a corona discharge by the catalytic action of nitrogen which is admixed to the reaction mixture as a constituent of air. A drawback of this process is that systems comprising a corona discharge are relatively bulky, expensive and consequently virtually unusable on a large industrial scale.

With respect to the relevant prior art reference is additionally made to a publication by B. Eliasson and U. Kogelschatz, Modeling and Application of Silent Discharge Plasmas, IEEE Transactions on Plasma Science, Vol. 19, No. 2, April 1991, pp. 309–323, which discloses a plurality of reactors arranged next to one another and above one another, involving silent electric discharge via a dielectric to generate ozone, which reactors can be employed in the present invention.

SUMMARY OF THE INVENTION

The invention as defined in the claims achieves the object of developing a process and an apparatus for converting a greenhouse gas, of the type mentioned at the outset, in such a way that more efficient production of fuels from an undesirable greenhouse gas becomes possible.

Advantageous refinements of the invention are defined in the dependent claims.

An advantage of the invention is that these fuels can be produced on a large industrial scale while requiring less energy input.

According to an advantageous refinement of the invention, CO and $H_2$ can be produced from a greenhouse gas in a 1st process stage and can be converted, in a 2nd process stage, into the desirable fuels. Consequently the use of hydrogen as a starting material can be dispensed with.

BRIEF DESCRIPTION OF THE DRAWINGS

The invention is explained below with reference to illustrative embodiments. In the figures.

DESCRIPTION OF THE PREFERRED EMBODIMENTS

In the figures, identical components are designated by identical reference symbols.

Figure 1:
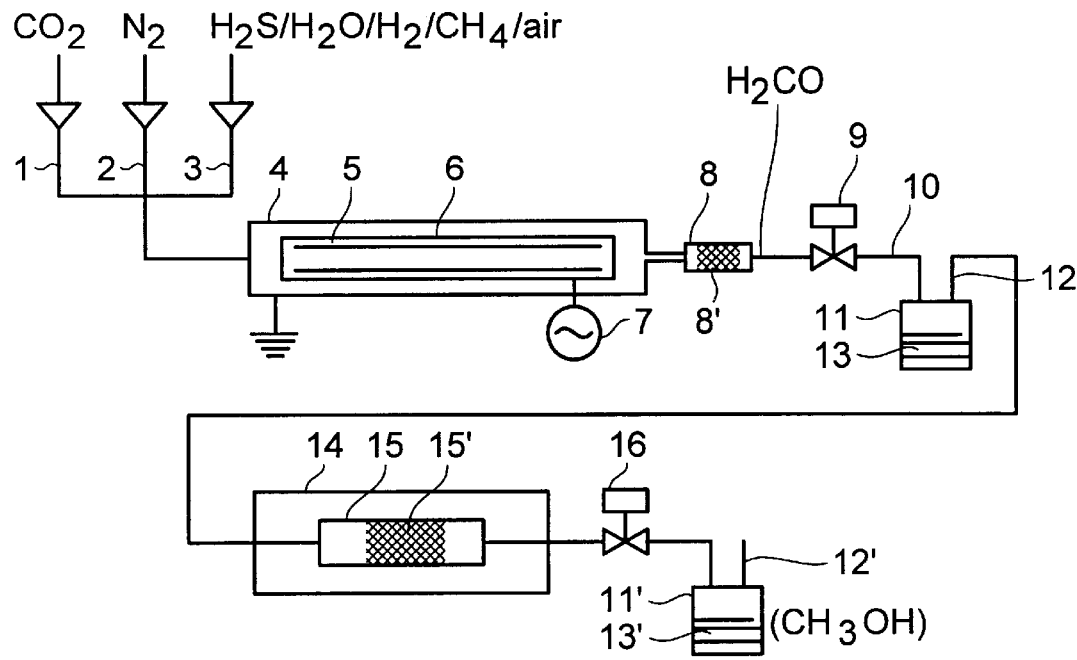
FIG. 1 shows a hybrid reactor comprising an electric and a downstream thermal reactor, FIG. 2 schematically shows a cellular structure of a hybrid reactor combined in one container, and FIG. 3 schematically shows the cellular structure of the hybrid reactor according to FIG. 2 comprising a.c. electrodes.

As depicted in FIG. 1, at least one greenhouse gas such as e.g. $CO_2$ and/or $CH_4$ and/or $N_2O$ and/or ozone, which may contribute to heating of the earth's atmosphere via the undesirable greenhouse effect, is fed, via a 1st gas supply line (1), to a 1st electric reactor (4) comprising a pressure-proof, earthed metal container or steel tube, which at the same time serves as its outer electrode.

Via a 2nd gas supply line (2), the 1st reactor (4) is fed with a reaction accelerator in the form of at least one 2nd energy-storing gas or gas mixture, i.e. a catalyst gas, which after a relaxation time transfers energy to at least one greenhouse reactant. Examples of reaction-accelerating catalyst gases which can be used include e.g. $N_2$, $N_2O$, air or a noble gas, preference being given to $N_2$, however.

Via a 3rd gas supply line (3), the 1st reactor (4) is fed with at least one hydrogen-containing gas such as e.g. $H_2$, $H_2S$, $CH_4$, air or a hydrogen-containing vapour, $H_2O$, or a chlorofluorocarbon or a hydro-chlorofluorocarbon, HCFC, as a coreactant for the greenhouse gas.

Inside said 1st reactor (4) there is at least one dielectric or a dielectric hollow body or a quartz tube (6) which is closed on one side in the inflow direction of the gases, with an inner electrode (5) made of a readily conductive corrosion-resistant metal or of an electroconductive layer or metal alloy, preferably of a thin gold layer. To this end, a gold-containing fluid was painted onto the inner wall of the quartz tube (6) and then stoved. This inner electrode (5) is electrically connected at its end to an a.c. voltage source (7) having an a.c. voltage in the range of 5 kV–50 kV and a frequency in the range of 50 Hz–1 MHz, preferably having an a.c. voltage in the range of 5 kV–25 kV and a frequency in the range of 1 kHz–100 kHz.

The distance between the outer cylindrical surface of the quartz tube (6) and the inner cylindrical surface of the steel tube of the 1st reactor (4) is in the range of from 0.5 mm to 3 mm, and is preferably 1 mm. Through this gap between the outer cylindrical surface of the quartz tube (6) and the inner cylindrical surface of the steel tube of the 1st reactor (4), the gas flows from left to right through the 1st reactor (4) and in the process is subjected to a so-called silent discharge, i.e. a low-current gas discharge which is fed from the electric a.c.

voltage source (7) via the dielectric (6), in the course of which gas discharge the atoms of the gases are excited or ionized, as described in the abovementioned publication in IEEE Transactions on Plasma Science, Vol. 19, No. 2, April 1991, pp. 309–323.

The nitrogen molecules, in particular, excited in the gas discharge are able to effect an extremely efficient, resonant energy transfer to $CO_2$ molecules present. The 1st excited vibration level (wavenumber 2331 $cm^{-1}$) of the nitrogen molecule has virtually the same energy level as the 1st excitation level (wavenumber 2349 $cm^{-1}$) of the asymmetric stretching vibration of the $CO_2$ molecule. Since it would be desirable, for efficient hydrogenation, for the $CO_2$ molecules first to be raised to an excited level, or even to be dissociated, this process may likewise involve the use of nitrogen or atoms or molecules of a similar type as a reaction accelerator.

On the output side the 1st reactor (4) is connected, via a 1st catalyst reactor (8), to an expansion valve (9) which, on the output side, is connected via a gas line or conduit (10) to a condensate separator or liquid vessel (11). The 1st catalyst reactor (8) contains a 1st catalyst (8'), preferably comprising a copper-containing material, e.g. containing CuO and ZnO on glass wool or quartz wool, at a temperature in the temperature range of 200° C.–300° C. and at a pressure in a pressure range of 100 kPa–10 MPa. Excited atoms and/or molecules and/or free radicals emerging from the 1st reactor (4) into the 1st catalyst reactor (8) are able to activate the 1st catalyst (8') even at relatively low temperatures. In the process, $CO_2$ is converted into CO and hydrogen-containing compounds are converted into $H_2$ and/or H.

Alternatively, the 1st catalyst (8') may be situated within the 1st reactor (4), so that a separate catalyst reactor (8) is unnecessary. The waste heat from the silent discharge in the 1st reactor (4) can then be used for heating the 1st catalyst (8').

The expansion of the gases downstream of the expansion valve (9) causes a liquid (13) comprising reaction products such as e.g. methanol and other hydrocarbon compounds, which can be used as fuels, to separate in the liquid vessel (11). Gases leaving the liquid vessel (11) via a gas offtake (12) are supplied to a 2nd or thermal reactor (14) which contains a 2nd catalyst (15') whose composition may correspond to that of the 1st catalyst (8'). This thermal reactor (14) is connected on its output side, via an expansion valve (16), to a liquid vessel (11') in which a reaction fluid (13') separates, e.g. $CH_3OH$. The 2nd catalyst (15') is operated at a temperature in the temperature range of 200° C.–300° C., preferably at a temperature in the temperature range of 200° C.–240° C. and at a pressure in a pressure range of <3 MPa, preferably in a pressure range of 100 kPa–2 MPa. Via a gas offtake (12'), gases which have not condensed in the liquid vessel (11') are vented; alternatively, they may be fed to one or more further thermal reactors (14) each 110 having a downstream expansion valve (16) and liquid vessel (11') (not shown). Of course, the reaction products and gases may be monitored by means of a gas chromatograph and/or some other analytical instrument (not shown).

Figure 2:
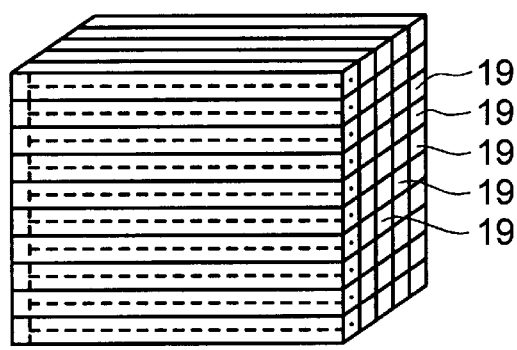

Since the life of the excited and/or ionized reactants is very short, it is advantageous for both 1st and 2nd reactors (4) and (14) to be combined in a container comprising a plurality of reaction chambers (19) disposed next to one another and on top of one another, as indicated in FIG. 2.

Figure 3:
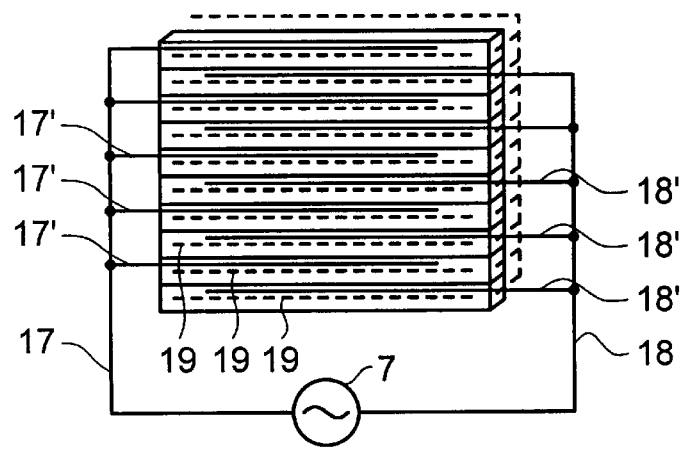

In this arrangement, the a.c. voltage source (7) is electrically connected, via 1st and 2nd a.c. voltage lines (17) and (18), to 1st and 2nd a.c. voltage electrodes (17') and (18'), which project, from different sides, into adjacent reaction chambers (19), compare FIG. 3. The walls of the reaction chambers (19) in this arrangement contain a catalyst and act as a dielectric barrier between the 1st and 2nd a.c. voltage electrodes (17') and (18'). This of course assumes that the catalyst is made of insulating material, as is the case for many oxide catalysts.

If electroconductive catalysts are used, however, the 1st and 2nd a.c. voltage electrodes (17') and (18') must be coated with a dielectric layer.

In the two arrangements, as described, according to FIG. 3 the excited atoms and/or molecules are formed in the direct vicinity of the catalyst walls, so that it is possible to operate at much lower temperatures and the catalysts are more efficient.

The volume fraction of the at least one 2nd energy-storing catalyst gas or catalyst gas mixture, based on the total volume of the gases taking part in the conversion, is in the range of 0.1%–5%, preferably in the range of 0.1%–1%.

The electric reactor (4) in accordance with FIG. 1 may have a cellular structure as depicted in FIG. 3. The 2nd catalyst (15) in the thermal reactor (14) in accordance with FIG. 1 may have a cellular structure as depicted in FIG. 2.

Instead of the waste gases from the gas offtake (12') in the condensate separator (11') being vented, it is also possible for them to be recycled to the input of the 1st reactor (4).

LIST OF DESIGNATIONS List of designations

1–3 gas supply lines
4 1st reactor for electric discharges, metal container, steel tube, outer electrode
5 inner electrode of 4
6 quartz tube, dielectric layer between 4 and 5, dielectric
7 a.c. voltage source, high-voltage source
8 1st catalyst reactor
8' 1st catalyst
9, 16 expansion valves
10 conduit, gas line
11, 11' liquid vessel, condensate separator, receiver
12, 12' gas offtakes
13, 13' liquids, reaction products, reaction fluid
14 2nd reactor, thermal reactor
15 2nd catalyst reactor in 14
15' 2nd catalyst
17 1st a.c. voltage line
17' 1st a.c. voltage electrodes on 17
18 2nd a.c. voltage line
18' 2nd a.c. voltage electrodes on 18
19 reaction chambers

We claim:

1. Apparatus for converting at least one greenhouse gas into a chemically or industrially utilizable substance or into a chemically or industrially utilizable mixture of substances, (a) comprising at least one $1^{st}$ electric reactor (4) for energetically exciting the at least one greenhouse gas, which can be fed on the input side to the at least one $1^{st}$ reactor (4), and (b) comprising at least one thermal reactor (14) in effective connection with the at least one $1^{st}$ electric reactor (4), characterized (c) in that the 15' reactor (4) and the thermal reactor (14) are combined in a hybrid reactor, (d) in that the hybrid rector has at least 2 adjacent reaction chambers (19), (e) in that at least one a.c. voltage electrode (17', 18') is disposed in each reaction chamber (19), in such a way that the a.c. voltage electrodes (17', 18') of pairs of immediately adjacent reaction chambers (19) are connected to opposite terminals of an a.c. voltage source (7), (f) in that the walls of the reaction chambers (19) comprise at least one catalytic material, and (g) in that said a.c. voltage electrodes (17', 18') connected to opposite terminals of an a.c. voltage source (7) are separated from one another by a dielectric barrier.

2. Apparatus according to claim 1, characterized in that the at least one thermal reactor (14) contains a copper-containing 2nd catalyst (15).

3. Apparatus according to claim 1, characterized in that said catalytic material is electrically insulating or deposited on an insulator and acts as said dielectric barrier.

4. Apparatus according to claim 1, characterized in that said a.c. voltage electrodes (17',18') are coated with said dielectric barrier.

* * * * *